(12) United States Patent
Firke et al.

(10) Patent No.: US 8,981,110 B2
(45) Date of Patent: Mar. 17, 2015

(54) PROCESS FOR THE PREPARATION OF OLMESARTAN MEDOXOMIL

(75) Inventors: Rajendra Vishwanath Firke, Maharashtra (IN); Ujjwal Komalsing Sisodiya, Maharashtra (IN); Chandrakant Shriram Bhangale, Maharashtra (IN); Radhakrishna Bhikaji Shivdavkar, Maharashtra (IN); Himanshu Madhav Godbole, Maharashtra (IN); Girij Pal Singh, Maharashtra (IN)

(73) Assignee: Lupin Limited, Mumbai, Maharashtra (IN)

( * ) Notice: Subject to any disclaimer, the term of this patent is extended or adjusted under 35 U.S.C. 154(b) by 0 days.

(21) Appl. No.: 14/237,213

(22) PCT Filed: Jul. 31, 2012

(86) PCT No.: PCT/IB2012/053896
§ 371 (c)(1),
(2), (4) Date: Feb. 5, 2014

(87) PCT Pub. No.: WO2013/021312
PCT Pub. Date: Feb. 14, 2013

(65) Prior Publication Data
US 2014/0179930 A1  Jun. 26, 2014

(30) Foreign Application Priority Data
Aug. 5, 2011 (IN) .......................... 1041/KOL/2011

(51) Int. Cl.
*C07D 403/10* (2006.01)
*A61K 31/41* (2006.01)
*C07D 405/14* (2006.01)

(52) U.S. Cl.
CPC .................................. *C07D 405/14* (2013.01)
USPC .......................................... 548/253; 514/381

(58) Field of Classification Search
None
See application file for complete search history.

(56) References Cited

U.S. PATENT DOCUMENTS

| 5,616,599 | A  | 4/1997 | Yanagisawa et al. |
|---|---|---|---|
| 7,528,258 | B2 | 5/2009 | Hedvati et al. |
| 2006/0074117 | A1 | 4/2006 | Hedvati et al. |
| 2008/0214637 | A1 | 9/2008 | Antoncic et al. |
| 2010/0076200 | A1 | 3/2010 | Hedvati et al. |

FOREIGN PATENT DOCUMENTS

| EP | 2 022 790 | 11/2009 |
|---|---|---|
| WO | WO 2006/073519 | 7/2006 |
| WO | WO 2007/017135 | 2/2007 |
| WO | WO 2007/048361 | 5/2007 |
| WO | WO 2008/043996 | 4/2008 |
| WO | WO 2010/067913 | 6/2010 |
| WO | WO 2011/014611 | 2/2011 |

OTHER PUBLICATIONS

International Search Report and Written Opinion from International Application No. PCT/IB2012/053896 mailed Oct. 19, 2012.
Park et al., "Novel amides and esters prodrugs of olmesartan: Synthesis, bioconversion and pharmacokinetic evaluation", *Bioorganic & Medicinal Chemistry Letters*, vol. 20, 2010, pp. 5895-5899.
Pati et al., "A Convenient and Practical Synthesis of Olmesartan Medoxomil Methyl Ether", *J. Heterocyclic Chem.*, vol. 45, 2008, pp. 917-920.
Srimurugan et al., "Unusual Detritylation of Tritylated Tetrazole in Sartan Molecules", *Chem. Pharm. Bull.*, vol. 56, No. 3, 2008, pp. 383-384.

*Primary Examiner* — Nyeemah A Grazier
(74) *Attorney, Agent, or Firm* — Merchant & Gould P.C.

(57) ABSTRACT

The present invention provides novel process for preparation of olmesartan medoxomil (I) substantially free of olmesartan acid impurity (II) comprising, reacting trityl olmesartan medoxomil (III) with acid, filtering the precipitate of trityl alcohol, subjecting the filtrate to agitated thin film drying and recovering olmesartan medoxomil (I).

15 Claims, No Drawings

PROCESS FOR THE PREPARATION OF OLMESARTAN MEDOXOMIL

This application is a National Stage Application of PCT/IB2012/053896, filed 31 Jul. 2012, which claims benefit of Serial No. 1041/KOL/2011, filed 5 Aug. 2011 in India and which applications are incorporated herein by reference. To the extent appropriate, a claim of priority is made to each of the above disclosed applications.

FIELD OF INVENTION

The present invention relates to novel process for preparation of olmesartan medoxomil (I) substantially free of olmesartan acid impurity (II).

BACKGROUND OF THE INVENTION

Olmesartan medoxomil is chemically known as 4-(1-hydroxy-1-methylethyl)-2-propyl-1-[[2'-(1H-tetrazol-5-yl)[1,1'-biphenyl]-4-yl]methyl]-1H-imidazole-5-carboxylic acid (5-methyl-2-oxo-1,3-dioxol-4-yl)methyl ester and represented by formula I

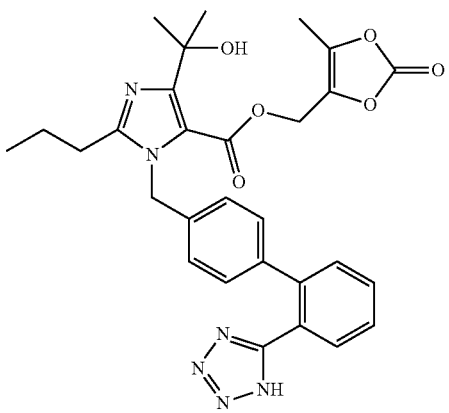

Olmesaratan medoxomil (I) is a prodrug that is selective $AT_1$ subtype angiotensin II receptor antagonist and pharmaceutically used as an antihypertensive for the treatment and prophylaxis of hypertension.

Olmesartan medoxomil (I) was first disclosed in U.S. Pat. No. 5,616,599, along with process for its preparation by treatment of trityl olmesartan medoxomil (III) with aqueous acetic acid. The filtrate obtained after removal of trityl alcohol was concentrated to give olmesartan medoxomil (I) containing about 4-5% of olmesartan acid impurity (II). This method is not industrially viable since, on a commercial scale the removal of large quantity of aqueous acetic acid would require longer durations causing higher rate of hydrolysis of olmesartan medoxomil (I) and producing excess of olmesartan acid impurity (II).

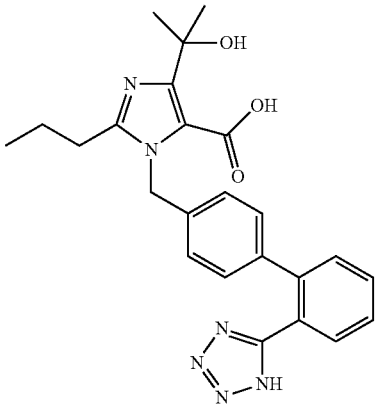

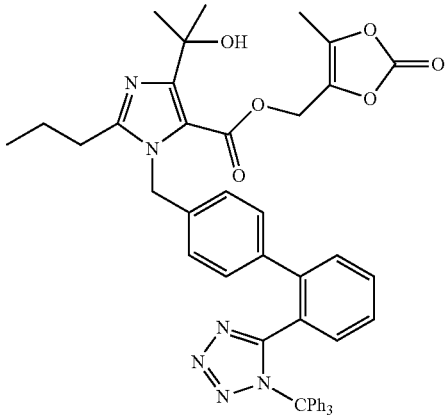

Another U.S. Pat. No. 7,528,258 provides process for preparation of olmesartan medoxomil (I) wherein trityl olmesartan medoxomil (III) is contacted with sulphuric acid in a water miscible organic solvent. The trityl alcohol was filtered off, base was added to the filtrate and olmesartan medoxomil (I) with about 1% of olmesartan acid impurity (II) was recovered. This method utilizes strong and corrosive acid like sulphuric acid and incorporate additional step of neutralizing the acid with a base.

Another application US 2008/0214637, describes process for preparation of olmesartan medoxomil (I), which involves reacting trityl olmesartan medoxomil (III) with catalytic amount of acid selected from trifluoroacetic acid, methanesulphonic acid etc. The process further involves pH adjustment of the reaction mixture utilizing a base followed by multiple extractions and concentration of solvents and thereafter recovery of product by crystallization/precipitation.

PCT application WO 2010/067913 describes process for preparation of olmesartan medoxomil (I) from trityl olmesartan (III), wherein the triphenylmethane group is removed by using an acidic cation exchange resin. This process involves resin which is pre-treated with acid and after the reaction the resin is filtered and the filtrate concentrated, the product is recovered by crystallization. This process involves additional steps like treating the resin with an acid, filtrations, recovery of the resin etc.

Patent applications US 2006/0074117 and US 2010/0076200 describes purification process to produce olmesartan medoxomil (I) containing less than 0.05% of olmesartan acid impurity (II), by crystallization from $C_{3-6}$ ketone-water mixture. However, this process utilizes excess volumes of solvents.

Thus, there exists a need for improved process for preparation of olmesartan medoxomil (I) that can avoid use of strong acid, multiple steps, laborious work-up, large excess of solvent volumes etc.

SUMMARY OF THE INVENTION

The present invention provides novel process for preparation of olmesartan medoxomil (I) substantially free of olmesartan acid impurity (II) comprising, reacting trityl olmesartan medoxomil (III) with an acid, filtering the precipitate of trityl alcohol, subjecting the filtrate to agitated thin film drying, recovering olmesartan medoxomil (I) and optionally crystallizing olmesartan medoxomil (I) from an organic solvent.

DETAILED DESCRIPTION OF THE INVENTION

In a preferred embodiment, the present invention provides novel process for preparation of olmesartan medoxomil (I) comprising:
a) reacting trityl olmesartan medoxomil (III) with an acid,
b) filtering the precipitate of trityl alcohol,
c) subjecting the filtrate to agitated thin film drying, and
d) recovering olmesartan medoxomil (I).

In another embodiment, the present invention provides novel process for preparation of olmesartan medoxomil (I) substantially free of olmesartan acid impurity (II) comprising:
a) reacting trityl olmesartan medoxomil (III) with an acid,
b) filtering the precipitate of trityl alcohol,
c) subjecting the filtrate to agitated thin film drying,
d) recovering olmesartan medoxomil (I), and
e) optionally crystallizing olmesartan medoxomil (I) from an organic solvent.

Olmesartan medoxomil (I) substantially free of olmesartan acid impurity (II) refers to compound (I) with less than 1%, preferably less than 0.5%, more preferably less than 0.1%, area percentage of HPLC of compound (II).

In the present invention, acid is selected from acetic acid, propionic acid, trifluoroacetic acid, hydrochloride acid etc., preferably acetic acid. Reaction of Step (a) is carried out in solvent selected from methanol, ethanol, acetone, ethyl acetate, tetrahydrofuran, 1,4-dioxane, water and mixtures thereof, preferably water. The reaction is carried out at a temperature of 0-100° C., preferably 20-60° C., more preferably 40-45° C.

The filtrate is subjected to evaporation in agitated thin film dryer (ATFD) under vacuum. The feed rate of the filtrate is maintained at 4 to 10 ml per minute. The heating medium is jacketed hot water of temperature of 40-90° C., preferably 45-50° C. The vacuum was maintained at 20-100 mm/Hg, preferably 70-75 mm/Hg.

The olmesartan medoxomil (I) was crystallized from an organic solvent selected from acetone, acetonitrile, ethyl acetate and mixtures thereof.

By using the present process olmesartan medoxomil (I) substantially free of olmesartan acid impurity (II) can be obtained since the process avoids distillation of the reaction mixture to remove aqueous acid unlike the prior art method. The U.S. Pat. No. 5,616,599 provides process in which the aqueous acetic acid is removed by concentration under reduced pressure, moreover to remove the traces of acetic acid and water, toluene is added and further concentrated. In this method the acidic reaction mixture is exposed to heat for longer duration causing hydrolysis of the product (I), therefore olmesartan medoxomil (I) obtained contains olmesartan acid impurity (II) in the range of 4-5 area percentage of HPLC.

During agitated thin film drying the aqueous organic acid is removed at a low temperature which avoids hydrolysis of olmesartan medoxomil (I) and results in olmesartan medoxomil (I) that is substantially free of olmesartan acid impurity (II).

The manufacture of olmesartan medoxomil (II) as per the process of present invention, has the following advantages over the prior art methods:
a. Process does not utilize strong and corrosive acids like sulphuric acid,
b. Process avoids multiple steps like pH adjustment, extractions and concentration of solvents etc,
c. Avoids use of resin and the multiple operating parameters related to it,
d. Avoids use of excess quantity of solvents for purification, and
e. Process is suitable for plant scale manufacture.

The present invention is further illustrated by the following representative examples and does not limit the scope of the invention.

EXAMPLES

Details of HPLC method:
Column: Waters symmetry C-8, 4.6×100 mm, 3.5 μm
Detector: UV at 250 nm
Column temp.: 40° C.
Buffer: 0.015 M monobasic potassium phosphate adjust pH with diluted (0.2%) phosphoric acid
Mobile phase:
 A) acetonitrile and buffer (1:4)
 B) acetonitrile and buffer (4:1)
Sample preparation: 1 mg/ml of olmesartan medoxomil in acetonitrile
Injection volume: 10 μl
Mode of elution: Gradiant
Flow: 1.0 ml/min
Run time: 55.0 minutes
Olmesartan acid impurity (II) has an RRT of 0.16 with respect to olmesartan medoxomil (I).

Example 1

Preparation Of Olmesartan Medoxomil (I) as per U.S. Pat. No. 5,616,599

To a mixture of acetic acid (76.8 ml) and water (25.6 ml) was added trityl olmesartan medoxomil (III) (10 g) and heated at 60° C. for 1.5 hours. Water (25.6 ml) was added and the reaction mixture was filtered to remove trityl alcohol. The filtrate was concentrated by rotary evaporator at 45-50° C., to the residual mass was added toluene (20 ml) and the mixture was concentrated at 45-50° C. Olmesartan medoxomil (I) thus obtained had HPLC purity: Olmesartan medoxomil (I) (92.41%); olmesartan acid impurity (II) (4.58%).

To the residue was added ethyl acetate (40 ml) and stirred at 25-30° for 1-2 hours and 0-5° for 1-2 hours. The solid was filtered, washed with ethyl acetate and dried. Yield 5.1 g (73.9%); HPLC purity: Olmesartan medoxomil (I) (94.11%); olmesartan acid impurity (II) (4.31%).

Example 2

Preparation of Olmesartan Medoxomil (I) as Per the Present Invention

To a mixture of acetic acid (37.5 ml) and water (12.5 ml) was added trityl olmesartan medoxomil (III) (10 g) and heated at 40-45° C. for 2 hours. Water (12.5 ml) was added and the reaction mixture was filtered to remove trityl alcohol. The filtrate was subjected to agitated thin film dryer, wherein the feed rate was of about 4 to 10 ml per minute, heating medium was jacketed hot water at 45-50° C. and vacuum was 70-75 mm/Hg. Crude olmesartan medoxomil (I) was recovered form ATFD. HPLC purity: olmesartan medoxomil (I) (97.81%); olmesartan acid impurity (II) (0.97%).

To acetone (40 ml) crude olmesartan medoxomil (I) was added, the slurry was heated at 54-58° C. for 30 minutes and then stirred for 1-2 hours at 0-5° C., the solid was filtered. Wet solid was added to acetone (120 ml) and heated at 55-60° C. The solution was filtered. From the filtrate about 95 ml of acetone was distilled out at atmospheric pressure. The concentrated mass was stirred at 25-30° C. for 8-12 hours and then at 0-5° C. for 1-3 hours. The solid was filtered, washed with acetone and dried. Yield 5.3 g (76.81%). HPLC purity: olmesartan medoxomil (I) (99.67%); olmesartan acid impurity (II) (0.07%).

We claim:

1. A process for preparation of olmesartan medoxomil (I) comprising:

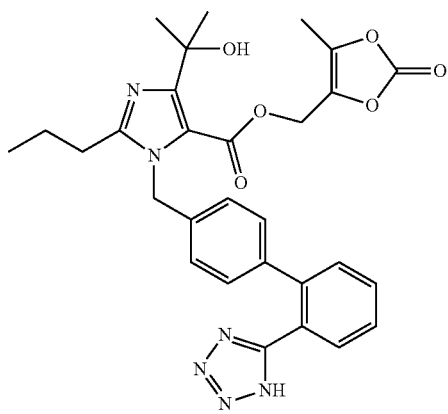
(I)

a) reacting trityl olmesartan medoxomil (III) with an acid,

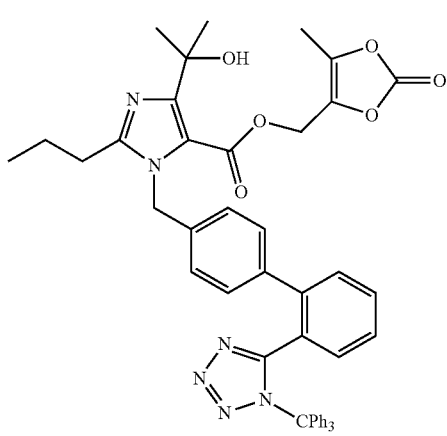
(III)

b) filtering the precipitate of trityl alcohol,
c) subjecting the filtrate to agitated thin film drying, and
d) recovering olmesartan medoxomil (I).

2. A process for preparation of olmesartan medoxomil (I) substantially free of olmesartan acid impurity (II) comprising:

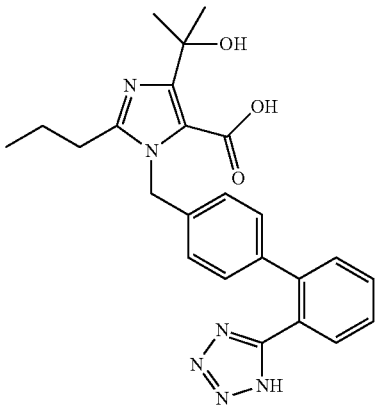
(II)

a) reacting trityl olmesartan medoxomil (III) with an acid,
b) filtering the precipitate of trityl alcohol,
c) subjecting the filtrate to agitated thin film drying,
d) recovering olmesartan medoxomil (I), and
e) optionally crystallizing olmesartan medoxomil (I) from an organic solvent.

3. A process according to claim 1 wherein, acid is selected from acetic acid, propionic acid, trifluoroacetic acid and hydrochloric acid.

4. A process according to claim 3 wherein, acid is acetic acid.

5. A process according to claim 1 wherein, step (a) is carried out in solvent selected from methanol, ethanol, acetone, ethyl acetate, tetrahydrofuran, 1,4-dioxane, water and mixtures thereof.

6. A process according to claim 5, wherein solvent is water.

7. A process according to claim 1 wherein, step (a) is carried out at a temperature of 0-100° C.

8. A process according to claim 7 wherein, temperature is 20-60° C.

9. A process according to claim 7 wherein, temperature is 40-45° C.

10. A process according to claim 1 wherein, the feed rate of subjecting the filtrate to agitated thin film dryer is at 4 to 10 ml per minute.

11. A process according to claim 1 wherein, heating medium for agitated thin film dryer is jacketed hot water of temperature of 40-90° C.

12. A process according to claim 11 wherein, temperature is 45-50° C.

13. A process according to claim 1 wherein, the agitated thin film drying is carried out at a vacuum of 20-100 mm/Hg.

14. A process according to claim 13 wherein, vacuum is 70-75 mm/Hg.

15. A process according to claim 2 wherein olmesartan medoxomil (I) is crystallized from an organic solvent selected from acetone, acetonitrile, ethyl acetate or mixtures thereof.

* * * * *